US007795205B2

(12) United States Patent
Yu

(10) Patent No.: US 7,795,205 B2
(45) Date of Patent: Sep. 14, 2010

(54) METHODS FOR EFFECTING REGRESSION OF TUMOR MASS AND SIZE IN A METASTASIZED PANCREATIC TUMOR

(75) Inventor: Cheng-Der Tony Yu, Baltimore, MD (US)

(73) Assignee: Canyon Pharmaceuticals, Inc., Hunt Valley, MD (US)

(*) Notice: Subject to any disclaimer, the term of this patent is extended or adjusted under 35 U.S.C. 154(b) by 221 days.

(21) Appl. No.: 11/099,370

(22) Filed: Apr. 4, 2005

(65) Prior Publication Data

US 2005/0233966 A1  Oct. 20, 2005

Related U.S. Application Data

(60) Provisional application No. 60/561,741, filed on Apr. 12, 2004.

(51) Int. Cl.
*A01N 37/18* (2006.01)
(52) U.S. Cl. .................................................. 514/2
(58) Field of Classification Search ............... 514/2
See application file for complete search history.

(56) References Cited

U.S. PATENT DOCUMENTS

| 4,346,078 A | 8/1982 | Bajusz et al. |
| 4,668,662 A | 5/1987 | Tripier |
| 4,703,036 A | 10/1987 | Bajusz et al. |
| 4,767,742 A | 8/1988 | Dodt et al. |
| 5,095,092 A | 3/1992 | Badziong et al. |
| 5,162,208 A | 11/1992 | Lemoine et al. |
| 5,180,668 A | 1/1993 | Crause et al. |
| 5,260,307 A | 11/1993 | Ackermann et al. |
| 5,405,854 A | 4/1995 | Ackermann et al. |
| 5,472,938 A | 12/1995 | Arvinte |
| 5,516,656 A | 5/1996 | Misawa et al. |
| 5,559,232 A | 9/1996 | Ackermann et al. |
| 5,726,043 A | 3/1998 | Heim et al. |
| 5,733,874 A | 3/1998 | Arvinte |
| 5,786,383 A | 7/1998 | Clement |
| 5,824,505 A | 10/1998 | Tolstoshev et al. |
| 5,843,925 A | 12/1998 | Backer et al. |
| 6,030,972 A | 2/2000 | Bohm et al. |
| 6,174,855 B1 | 1/2001 | Hansson |
| 6,284,751 B1 | 9/2001 | Aiello et al. |
| 6,436,901 B1 | 8/2002 | Arvinte |
| 6,455,671 B1 | 9/2002 | Bohm et al. |
| 6,573,256 B2 | 6/2003 | Bishop et al. |
| 6,627,731 B1 | 9/2003 | Carney et al. |
| 6,673,805 B2 * | 1/2004 | Lauria et al. ............ 514/283 |
| 6,696,483 B2 | 2/2004 | Singh |
| 2002/0173620 A1 | 11/2002 | Habermann |

FOREIGN PATENT DOCUMENTS

| AU | B-75366/87 | 9/1991 |
| CA | 1 341 426 | 4/2003 |
| EP | 0 195 212 A2 | 9/1986 |
| EP | 225 633 | 6/1987 |
| EP | 293 881 A2 | 12/1988 |
| EP | 0 341 215 A2 | 11/1989 |
| EP | 0 341 215 A3 | 11/1989 |
| EP | 0 352 227 A2 | 1/1990 |
| EP | 0 352 227 A3 | 1/1990 |
| EP | 0 352 228 A2 | 1/1990 |
| EP | 0 352 228 A3 | 1/1990 |
| EP | 0 362 002 A1 | 4/1990 |
| EP | 0 364 344 A2 | 4/1990 |
| EP | 0 364 344 A3 | 4/1990 |
| EP | 225633 B1 | 8/1992 |
| EP | 0503 829 A2 | 9/1992 |
| EP | 0 526 877 A2 | 2/1993 |
| EP | 0 526 877 A3 | 2/1993 |
| EP | 0 530 167 A1 | 3/1993 |
| EP | 0 542 525 A2 | 5/1993 |
| EP | 0 542 525 A3 | 5/1993 |
| EP | 0 648 780 A1 | 4/1995 |
| EP | 0 669 317 A1 | 8/1995 |
| EP | 0 601 459 A2 | 6/1996 |
| EP | 0 601 459 A3 | 6/1996 |
| EP | 0 686 642 A2 | 10/1996 |
| EP | 0 686 642 A3 | 10/1996 |
| IE | 67136 | 3/1996 |
| WO | WO 93/11152 A1 | 6/1993 |
| WO | WO 93/18060 A1 | 9/1993 |
| WO | WO 94/29336 | 12/1994 |
| WO | WO 9429336 | 12/1994 |
| WO | WO 9523609 | 9/1995 |
| WO | WO 9535309 | 12/1995 |
| WO | WO 9625426 | 8/1996 |

OTHER PUBLICATIONS

Bowie, et al. Science, vol. 247: 1306-1310, 1990.*

(Continued)

*Primary Examiner*—Larry R Helms
*Assistant Examiner*—Hong Sang
(74) *Attorney, Agent, or Firm*—Hogan Lovells US LLP

(57) ABSTRACT

The present invention relates generally to methods of inhibiting angiogenesis in a patient by administering an effective angiogenesis-inhibiting amount of a thrombin inhibitor, and to the treatment of disease states that result from uncontrolled cell proliferation by administering a thrombin inhibitor alone or co-administering a thrombin inhibitor with an anticancer or cytotoxic agent. Specifically, the thrombin inhibitors used in the methods of the present invention are hirudins.

13 Claims, No Drawings

OTHER PUBLICATIONS

Lazar, et al. Mol. Cell. Biol., 8(3): 1247-1252, 1988.*

Burgess, et al. J. Cell Biol. 111: 2129-2138, 1990.*

Ngo et al., in"The Protein Folding Problem and Tediary Structure Prediction", 1994, Merz, et al. (ed.), Birkhauser, Boston, MA, pp. 433, and 492-495.*

Bukowski et al., Cancer, 1982, 50:197-200.*

Carney, et al. "Role of Specific Cell Surface Receptors in Thrombin-Stimulated Cell Division", Cell, Dec. 1978, pp. 1341-1349, vol. 15, MIT.

Folkman, "How Is Blood Vessel Growth Regulated in Normal and Neoplastic Tissue?" Cancer Research, Feb. 1986, pp. 467-473, vol. 46, G. H. A. Clowes Memorial Award Lecture.

Tamargo, et al. "Angiogenesis Inhibition by Minocycline", Cancer Research, Jan. 15, 1991, pp. 672-675, vol. 51.

Teicher, et al. "Antiangiogenic Agents Potentiate Cytotoxic Cancer Therapies against Primary and Metastatic Disease", Cancer Research, Dec. 1, 1992, pp. 6702-6704, vol. 52.

Claeson, "Synthetic peptides and peptidomimetics as substrates and Inhibitors of thrombin and other proteases in the blood coagulation system", Blood Coagulation and Fibrinolysis, 1994, pp. 411-436, vol. 5, Rapid Communications of Oxford Ltd.

Tuong, et al. "Characterization of the Deamidated Forms of Recombinant Hirudin", Biochemistry, 1992, pp. 8291-8299, vol. 31, American Chemical Society.

Bundgaard, (edited by Krogsgaard-Larson and Bundgaard), "Design and Application of Prodrugs", A Textbook of Drug Design and Development, 1991, Chapter 5, pp. 113-191, Harwood Academic Publishers.

Bundgarrd, "(C) Means to Enhance Penetration (1) Prodrugs as a means to improve the delivery of peptide drugs", Advanced Drug Delivery Reviews, 1992, pp. 1-38, vol. 8, Elsevier Science Publishers B.V.

Nielsen, et al. "Glycolamide Esters as Biolabile Prodrugs of Carboxylic Acid Agents: Synthesis, Stability, Bioconversion, and Physicochemical Properties", Journal of Pharmaceutical Sciences, Apr. 1988, pp. 285-298, vol. 77, No. 4, American Pharmaceutical Association.

Kakeya, "Studies on Prodrugs of Cephalosporins. I. Synthesis and Biological Properties of Glycyloxybenzoyloxymethyl and Glycylaminobenzoyloxymethyl Esters of 7 β-[2-(2-Aminothiazol-4-yl)-(Z)-2-methoxyiminoacetamido]-3-methyl-3-cephem-4-carboxylic Acid", Chem. Pharm. Bull., 1984, pp. 692-698, vol. 32.

Hansch, "Comprehensive Medicinal Chemistry the Rational Design, Mechanistic Study & Therapeutic Application of Chemical Compounds", 1990, Chapter 25.3, vol. 5, Pergamon Press plc.

Henrikson, et al. "Role of thrombin receptor in breast cancer invasiveness"; British Journal of Cancer; Cancer Research Campaign; 1999; pp. 401-406; vol. 79(3/4).

Sadoff, et al. "Complete Clinical Remission in a Patient With Advanced Pancreatic Cancer Using Mitomycin C-Based Chemotherapy the Role of Adjunctive Heparin"; American Journal of Clinical Oncology; 1999; pp. 187-190; vol. 22(2); Lippincott Williams & Wilkins, Inc. Philadelphia.

Salzet; "Leech Thrombin Inhibitors"; Current Pharmaceutical Design; 2002; pp. 493-503; vol. 8; Bentham Science Publishers Ltd.

Robert, et al. "Phase II study of docetaxel plus enoxaparin in chemotherapy-naïve patients with metastatic non-small cell lung cancer: preliminary results"; Lung Cancer; 2003; pp. 237-245; vol. 42; Elsevier Ireland Ltd.

Weitz, et al. "Chemotherapy-Induced Activation of Hemostasis: Effect of a Low Molecular Weight Heparin (Dalteparin Sodium) on Plasma Markers of Hemostatic Activation"; Thromb Haemost; 2002; pp. 213-220; vol. 88; Schatauer GmbH; Stuttgart.

Lind, et al. "Correlates of thrombin generation in patients with advanced prostrate cancer"; Schattauer GmbH; 2003; pp. 185-189; Stuttgart.

Caunt, et al. "Thrombin induces neoangiogenesis in the chick chorioallantoic membrane"; Journal of Thrombosis and Hacmostasis; International Society on Thrombosis and Hacmostasis; May 2003; pp. 2097-2102; vol. 1.

Lee, et al. "Hirudin Inhibits Human Tumor Implantation and Metastasis in Nude Mice"Journal of Hematology; Blood; American Society of Hematology; Nov. 16, 2000; Abstract # 3534; 818a; vol. 96(11).

Standop, et al. "Experimental Animal Models in Pancreatic Carcinogenesis: Lessons for Human Pancreatic Cancer"; Digestive Diseases; S. Karger AG, Basel; 2001; pp. 24-31; vol. 19(1).

Friess, et al. "A randomized multi-center phase II trial of the angiogenesis inhibitor Cilengitide (EMD 121974) and gemcitabine compared with gemcitabine alone in advanced unresectable pancreatic cancer"; BMC Cancer; BioMed Central; 2006; pp. 1-12; vol. 6(285).

PCT International Search Report PCT/US05/11549.

Esumi, et al. "Inhibition of Murine Melanoma Experimental Metastasis by Recombinant Desulfatohirudin, a Highly Specific Thrombin Inhibitor"; Cancer Research; Sep. 1, 1991; pp. 4549-4556; vol. 51.

Allegrini, et al, "Thrombospondin-1 plus irinotecan: a novel antiangiogenic-chemotherapeutic combination that inhibits the growth of advanced human colon tumor xenografts in mice"; Cancer Chemother Pharmacol; 2004; pp. 261-266; vol. 53.

Lokich, et al. "Dose intensity for bolus versus Infusion chemotherapy administration: Review of the literature for 27 anti-neoplastic agents"; Annals of Oncology; 1997; pp. 15-25; vol. 8; Kluwer Academic Publishers; Netherlands.

Hitoshi, Yamahata, et al. "The role of thrombin in the neovascularization of malignant gliomas: an intrinsic modulator for the up-regulation of vascular endothelial growth factor." International Journal of Oncology, May 2002, vol. 20, No. 5, pp. 921-928.

Darmoul, D. et al. "Aberrant expression and activation of the thrombin receptor protease-activated receptor-1 induces cell proliferation and motility in human colon cancer cells." American Journal of Pathology, vol. 162, No. 5, Jan. 1, 2003, pp. 1503-1513.

Warkentin, Theodore E. "Bivalent direct thrombin inhibitors: hirudin and bivalirudin." Best Practice & Research. Clinical Hematology, Mar. 2004, vol. 17, No. 1, pp. 105-125.

Hu, Liang, et al. "Role of endogenous thrombin in tumor implantation, seeding, and spontaneous metastasis." Blood, Nov. 1, 2004. vol. 104, No. 9, pp. 2746-2751.

Supplementary European Search Report, Application No. EP05763698, Jul. 14, 2009, pp. 1-3.

Folkman, Judah, et al. "Angiogenesis Inhibition and Tumor Regression Caused by Heparin or Heparin Fragment in the Presence of Cortisone." Science, vol. 221, Aug. 19, 1983, pp. 719-725.

J.D. Berlin, et al., "Phase III Study of Gemcitabine in combination with Fluorouracil Versus Gemcitabine . . . ", J. Clinical Oncology, vol. 20, No. 15, Aug. 1, 2002, pp. 3270-3275.

C.M. Rocha Lima, et al., "Irinatecan Plus Gemcitabine Results in No Survival . . . ", J. Clinical Oncology, vol. 22, No. 18, Sep. 15, 2004, pp. 3376-3383.

G.K. Abou-Alfa, et al., "Randomized Phase II Study of Exatecan . . . ", J. Clinical Oncology, vol. 24, No. 27, Sep. 20, 2006, pp. 4441-4447.

R. Herrmann, et al., "Gemcitabine Plus Capecitabine Compared with . . . ", J. Clinical Oncology, vol. 25, No. 16, Jun. 1, 2007, pp. 2212-2217.

C. Louvet, et al., "Gemcitabine in Combination with Oxaliplatin . . . ", J. Clinical Oncology, vol. 23, No. 15, May 20, 2005, pp. 3509-3516.

E. Van Cutsem, et al., "Plase II Trial of Gemcitabine Plus Tipfarnib . . . ", J. Clinical Oncology, vol. 22, No. 8, Apr. 15, 2004, pp. 14330-14338.

H. Oettle, et al., "A Phase III Trial of Pemetrexed Plus Gemcitabine . . . ", Annals of Oncology, vol. 16, Aug. 8, 2005, pp. 1639-1645.

http://seer.cancer.gov/statfacts/html/pancreas.html, Surveillance, Epidemiology and End Results Program of the Nat'l Cancer Institute, U.S. Nat'l Inst. Of Health, Nov. 2009.

* cited by examiner

METHODS FOR EFFECTING REGRESSION OF TUMOR MASS AND SIZE IN A METASTASIZED PANCREATIC TUMOR

RELATED APPLICATION

The present invention claims priority of U.S. Provisional Application No. 60/561,741 filed Apr. 12, 2004, which is incorporated herein in its entirety by this referenced.

BACKGROUND OF THE INVENTION

1. Field of the Invention

The present invention relates generally to methods of inhibiting angiogenesis in a patient by administering an effective angiogenesis-inhibiting amount of a thrombin inhibitor, and to the treatment of disease states that result from uncontrolled cell proliferation by administering a thrombin inhibitor alone or co-administering a thrombin inhibitor with an anticancer or cytotoxic agent. Specifically, the thrombin inhibitors used in the methods of the present invention are hirudins.

2. Discussion of the Related Art

The circulatory system serves an important role in the transport of nutrients, proteins, hormones, and other vital molecules that are necessary to maintain life. Blood vessels, which form an intricate network of pathways, represent an integral component of the circulatory system. In mammalian species, the internal surface of a blood vessel lumen is comprised of endothelial cells. These endothelial cells impart a smooth and low resistance quality to the lumenal surface. Critical to the free flow and transport of blood and blood constituents, the smooth and nonadhesive internal surface of the blood vessel increases the ease with which fluid flows. Without a smooth internal surface, blood vessels would become obstructed due to the formation of thrombi or other blockages at "sticky" locations on the internal walls. Complete or even partial blood vessel blockage would cause restriction of blood flow, thereby compromising the viability of living tissue served by the vessel. Thus, endothelial cells represent an important structural component of blood vessels and also provide blood vessels with a smooth internal surface.

The formation of blood vessels in vivo takes place in response to stimuli, which are provided in the form of specialized growth factors. These growth factors induce mitosis in cells already present in blood vessels. The new cells may replace nearby damaged cells, or the new cells may arrange themselves such that new blood vessels are formed. The process of growing blood vessels from endothelial cells is termed "angiogenesis," which results in, among other characteristics, the vascularization of tissue.

Thrombin may play a role in metastasis and angiogenesis of tumors. Generally, for a tumor to grow larger than a few millimeters in diameter, vascular endothelium must proliferate and form vesicle walls to provide circulation and nutrients to the cells inside of the tumor mass. Thrombin likely potentiates this process by virtue of its ability to induce proliferation of endothelial cells. In addition, thrombin has been shown to disrupt the normal intercellular endothelial cell contacts important in preventing cells and plasma factors from escaping or entering the microvasculature. The present hypothesis that thrombin may increase metastasis by disrupting these contacts is supported by studies demonstrating a correlation between decreased levels of anti-thrombin III (which removes thrombin and other proteases from plasma) and increased tumor metastasis.

Cancerous cells derive from a single cell that has mutated in a way that permits it to escape from the biochemical controls that limit the multiplication of normal cells. Once that cell fails to respond normally to growth inhibitors, it starts to proliferate. When the growing tumor reaches a certain diameter, however, simple diffusion in and out of the tumor tissue no longer suffices to supply oxygen and nutrients and remove waste. Further growth depends on angiogenesis (i.e., the formation of new blood vessels from the existing vascular bed), and the small tumor must produce factors that stimulate the growth of blood vessels. Therefore, the inhibition of angiogenesis, in turn leads to the decrease of proliferation of malignant and neoplastic cells.

Carney, et al., *Cell,* 15:1341 (1978) have postulated that high-affinity cell surface thrombin receptors may be involved in tumor metastasis and angiogenesis. For example, studies have indicated that thrombin receptors can serve as binding sites for tissue plasminogen activator, a molecule secreted from metastatic tumor cells. Moreover, other studies demonstrate the involvement of tissue plasminogen activator in metastasis and angiogenesis. Thus, many of the effects of plasminogen activator may be mediated through its interaction with the cell surface thrombin receptor. Carney, et al., have therefore proposed that stimulation of the thrombin receptor serves to promote tumor metastases, while inhibition of the receptor will decrease metastatic activity.

Angiogenesis has become a central theme in promoting the understanding of how tissue grows. As indicated above, endothelial cell proliferation is not only desirable, but also necessary to carry out a number of physiological processes, for example the in utero formation of tissues and organs. In other contexts, however, angiogenesis may be harmful to the overall health of an organism. For example, angiogenesis makes tumor growth and metastasis possible by vascularizing the tumor, thereby supplying the tumor with blood and nutrients that are necessary to sustain the tumor's growth, as well as providing routes by which tumor cells can migrate to distant parts of the body. (Folkman *Cancer Res.* 46(2):467-473 (1986). Clearly then, the prevention or reduction of angiogenesis may be a desirable goal in treating some disorders and diseases. Compounds have been tested for their ability to inhibit or reduce angiogenesis. Inhibitors of vascular endothelial growth factor (VEGF), a protein that selectively induces mitosis of vascular endothelial cells, have been investigated. For example, U.S. Pat. No. 6,284,751 to Aiello, et al., describes using inhibitors of the beta isozyme of protein kinase C to counteract the effects of VEGF. Antibiotics such as minocycline have also been reported to inhibit angiogenesis. Some investigators have reported inhibition of tumor growth as well as reduction in the number of metastatic tumors following administration of minocycline in combination with radiation or chemotherapy. See Tamargo, et al. *Cancer Res.,* 51(2):672-675 (1991), and Teicher, *Cancer Res.,* 52(23):6702-6704 (1992). U.S. Pat. No. 5,843,925 to Backer, et al., describes inhibition of angiogenesis upon administration of certain deoxytetracylines. Many of these angiogenesis-inhibiting compounds, however, have only been tested in vitro for their antiproliferative activity.

Thus, there is a need to identify additional compounds as inhibitors of angiogenesis.

SUMMARY OF THE INVENTION

The present invention provides methods and compositions for treating diseases and processes mediated by undesired and uncontrolled angiogenesis by administering to a patient with the undesired angiogenesis a composition comprising a thrombin inhibitor, in a dosage sufficient to inhibit angiogenesis. In one embodiment, the angiogenesis is associated with a cellular proliferative disease. In particular, the invention provides a method of treating angiogenesis-dependent cancer in patients. The present invention is particularly useful for treating or for repressing the growth of tumors. For example, administration of desulphatohirudin to a human or animal with prevascularized metastasized tumors prevents the growth or expansion of those tumors.

The present invention provides methods and compositions for treating diseases and processes mediated by undesired and uncontrolled angiogenesis by administering to a patient with the undesired angiogenesis a composition comprising hirudin in a dosage sufficient to inhibit angiogenesis. In particular, the invention provides a method of treating angiogenesis-dependent cancer in patients, and for curing angiogenesis-dependent cancer in patients. In one embodiment, the angiogenesis is associated with a cellular proliferative disease.

The present invention provides methods and compositions for treating diseases and processes mediated by undesired and uncontrolled angiogenesis by administering to a patient with the undesired angiogenesis a composition comprising desulphatohirudin in a dosage sufficient to inhibit angiogenesis. In particular, the invention provides a method of treating angiogenesis-dependent cancer in patients, and for curing angiogenesis-dependent cancer in patients. In one embodiment, the angiogenesis is associated with a cellular proliferative disease.

The present invention provides methods and compositions for treating cancer by administering to a patient a composition comprising co-administering desulphatohirudin with a cytotoxic or anticancer agent. The present invention is particularly useful for treating or for repressing the growth of tumors. For example, administration of desulphatohirudin to a human or animal with prevascularized metastasized tumors prevents the growth or expansion of those tumors.

Another aspect of the present invention provides methods and compositions for treating cancer by administering to a patient a composition comprising co-administering desulphatohirudin with a cytotoxic or anticancer agent.

The present invention further provides pharmaceutical formulations to treat a patient in need of anti-angiogenic or anticancer therapy, wherein the formulation is comprised of a pharmaceutically acceptable solvent, a pharmaceutically acceptable carrier, and desulphatohirudin in a quantity effective to inhibit angiogenesis. The solvent may be aqueous or nonaqueous and may also be organic or inorganic. The solvent may be packaged in a separate container and be added to the desulphatohirudin prior to administration. The desulphatohirudin may be formulated as a lyophilized dry product. In another embodiment, the formulation further comprises potassium phosphate. In yet another embodiment, the formulation further comprises a sugar. In yet another embodiment, the formulation further comprises a divalent or trivalent metal ion.

DETAILED DESCRIPTION OF THE INVENTION

The present invention provides methods and compositions for treating diseases and processes mediated by undesired and uncontrolled angiogenesis by administering to a patient with the undesired angiogenesis a pharmaceutical composition comprising a thrombin inhibitor in a dosage sufficient to inhibit angiogenesis. In one embodiment, the angiogenesis is associated with a cellular proliferative disease. In particular, the invention provides a method of treating angiogenesis-dependent cancer in patients, comprising administering desulphatohirudin or desirudin along or as an adjuvant to chemotherapy.

The term "cellular proliferative disease" is intended to refer to any condition characterized by the undesired propagation of cells. Included are conditions such as neoplasms, cancers, and tumors. "Cellular proliferative diseases" also include non-cancerous conditions such as benign melanomas, benign prostatic hyperplasia, psoriasis, and other cellular growths occurring within the epidermal layers.

"Cancer" means angiogenesis-dependent cancers and tumors, i.e., tumors that require for their growth (expansion in volume and/or mass) an increase in the number and density of the blood vessels supplying them with blood.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, for example, "treating" a patient involves prevention of a particular disorder or adverse physiological event in a susceptible individual as well as treatment of a clinically symptomatic individual by inhibiting or causing regression of a disorder or disease. Thus, for example, the present method of "treating" a patient in need of anti-angiogenic therapy encompasses both prevention of a condition, disease, or disorder that is responsive to anti-angiogenic therapy and treatment of a condition, disease, or disorder that is responsive to anti-angiogenic therapy in a clinically symptomatic individual.

"Regression" refers to the reduction of tumor mass and size.

"Patient" as used herein refers to a mammalian, preferably human, individual who can benefit from the pharmaceutical formulations and methods of the present invention. There is no limitation on the type of mammal that could benefit from the presently described pharmaceutical formulations and methods.

By the terms "effective amount" or "therapeutically effective amount" of an agent as used herein are meant a sufficient amount of the agent to provide the desired therapeutic effect. Furthermore, an "effective angiogenesis-inhibiting amount" of an agent is a sufficient amount of the agent to at least partially inhibit angiogenesis. Of course, undesirable effects, e.g., side effects, are sometimes manifested along with the desired therapeutic effect; hence a practitioner balances the potential benefits against the potential risks in determining what is an appropriate "effective amount." As will be pointed out below, the exact amount required will vary from subject to subject, depending on the species, age, and general condition of the subject, mode of administration, and the like. Thus, it is not possible to specify an exact "effective amount." However, an appropriate "effective amount" or "effective angiogenesis-inhibiting amount" in any individual case may be determined by one of ordinary skill in the art using only routine experimentation.

I. The Pharmaceutical Formulation

One aspect of the invention provides a pharmaceutical formulation for treating a patient in need of anti-angiogenic therapy comprising a thrombin inhibitor in an amount effective to inhibit angiogenesis and a pharmaceutically acceptable carrier.

A. Active Agent

In the past few years cDNAs and synthetic genes coding for hirudin variants have been cloned and expressed in microbial hosts, such as but not limited to *E. coli* and yeast. The expression products in yeast (*Saccharomyces cerevisiae*, strain TY 1456) lack the sulphate monoester group at Tyr$^{63}$—and were therefore designated "desulphatohirudins"—they turned out to exhibit approximately the same biological activity as the natural, sulphated hirudins. Desulphatohirudin variant HV1 has been expressed in *Escherichia coli* (European Patent Nos. 158 564 and 168 342) and in *Saccharomyces cerevisiae* (European Patent No. 168 342, 200 655, 225 633, 252 854 and 341 215). Similarly, desulphatohirudin HV2 has been expressed in *Escherichia coli* (European Patent No. 158 564) and in *Saccharomyces cerevisiae* (European Patent No. 200 655, PCT-Application No. 86/01224] and des-(Val)$_2$-desulphatohirudin has been expressed in *Escherichia coli* (European Patent No. 158 986).

According to the present invention, the term "hirudin" is intended to embrace desulphathohirudin, a hirudin variant or a desulphatohirudin variant or a mutant thereof, respectively, described in the literature and in particular a desulphatohirudin compound or a mutant thereof obtainable from a transformed microorganism strain containing DNA which codes for a desulphatohirudin or a mutant thereof. Such desulphatohirudins are, for example, desulphatohirudin variant HV1, HV1 modified (a, b), HV2, HV2 modified (a, b, c), HV3, variants of HV3 and des (Val$_2$)-desulphatohirudin. Also included are synthetic forms such as hirulogs and low molecular weight peptide-based thrombin inhibitors.

Preferred desulphatohirudins are those having the formula I (SEQ ID NO: 1):

```
Val Val Tyr Thr Asp Cys Thr Glu Ser Gly Gln Asn Leu Cys Leu Cys    (I)
 1               5                   10                  15

Glu Gly Ser Asn Val Cys Gly Gln Gly Asn Xaa Cys Ile Leu Gly Ser
            20                  25                  30

Asp Gly Glu Xaa Asn Gln Cys Val Thr Gly Glu Gly Thr Pro Xaa Pro
            35              40                  45

Gln Ser Xaa Asn Asp Gly Asp Phe Glu Glu Ile Pro Glu Xaa Xaa Xaa
        50              55                  60

Xaa Xaa
65
``` in which
a) Xaa at 27, 36 and 47 are each Lys, Xaa at 51 is His and Xaa at 62-65 is the peptide residue Glu-Tyr-Leu-Gln (SEQ ID NO:2) Xaa at 66 not present, (HV1) or
b) Xaa at 27 is Ile or Glu and Xaa at 36, 47, 51 and 62-66 are as defined in a) (HV1 modified a), or
c) Xaa at 36 is Ile or Glu and Xaa at 27, 47, 51 and 62-66 are as defined in a) (HV1 modified a), or
d) Xaa at 47 is Ile or Glu and Xaa at 27, 36, 51 and 62-66 are as defined in a) (HV1 modified a), or
e) Xaa at 51 is Leu or Asp and Xaa at 27, 36, 47 and 62-66 are as defined in a) (HV1 modified a), or
f) Xaa at 62-66 is selected from the group consisting of Glu-Tyr (Xaa at 64-66 not present), Glu-Tyr-Leu (Xaa at 65-66 not present), Glu-Asp-Leu-Gln (SEQ ID NO:3) (Xaa at 66 not present), Glu-Glu-Leu-Gln (SEQ ID NO:4) (Xaa at 66 not present), Glu-Tyr-Lys-Arg (SEQ ID NO:5) (Xaa at 66 not present), Glu-Asp-Lys-Arg (SEQ ID NO:6) (Xaa at 66 not present), Glu-Lys-Leu-Gln (SEQ ID NO:7) (Xaa at 66 not present), Ser-Phe-Arg-Tyr (SEQ ID NO:8) (Xaa at 66 not present), Trp-Glu-Leu-Arg (SEQ ID NO:9) (Xaa at 66 not present), Glu-Tyr-Leu-Gln-Pro (SEQ ID NO:10) and Glu-Tyr-Leu-Gln-Arg (SEQ ID NO:11) and Xaa at 27, 36, 47 and 51 are as defined in a) (HV1 modified b), or having the formula II (SEQ ID NO: 12)

```
Leu Thr Tyr Thr Asp Cys Thr Glu Ser Gly Gln Asn Leu Cys Leu Cys    (II)
 1               5                   10                  15

Glu Gly Ser Asn Val Cys Gly Gln Gly Asn Lys Cys Ile Leu Gly Ser
            20                  25                  30

Asp Gly Glu Lys Asn Gln Cys Val Thr Gly Glu Gly Thr Pro Lys Pro
            35              40                  45

Gln Ser His Asn Asp Gly Asp Phe Glu Glu Ile Pro Glu Glu Tyr Leu Gln
        50              55                  60                  65
``` or having the formula III (SEQ ID NO: 13)

```
Ile Thr Tyr Thr Asp Cys Thr Glu Ser Gly Gln Asn Leu Cys Leu Cys    (III)
 1               5                                       15

Glu Gly Ser Asn Val Cys Gly Lys Gly Asn Lys Cys Ile Leu Gly Ser
            20                  25                  30

Asn Gly Lys Gly Asn Gln Cys Val Thr Gly Glu Gly Thr Pro Xaa Pro
            35              40                  45

Glu Ser His Asn Asn Gly Asp Phe Glu Glu Ile Pro Glu Glu Xaa Leu Gln
        50              55                  60                  65
``` in which
a) Xaa at 47 is Asn and Xaa at 63 is Tyr (HV2), or
b) Xaa at 47 is Lys, Arg or His and Xaa at 63 is Tyr (HV2 modified a), or
c) Xaa at 63 is Glu or Asp and Xaa at 47 is Asn (HV2 modified b), or having the formula IV (SEQ ID NO: 14)

```
Val Val Tyr Thr Asp Cys Thr Glu Ser Gly Gln Asn Leu Cys Leu Cys      (IV)
1               5                   10                  15

Glu Gly Ser Asn Val Cys Gly Lys Gly Asn Lys Cys Ile Leu Gly Ser
            20                  25                  30

Asn Gly Lys Gly Asn Gln Cys Val Thr Gly Glu Gly Thr Pro Asn Pro
        35                  40                  45

Glu Ser His Asn Asn Gly Asp Phe Glu Glu Ile Pro Glu Glu Tyr Leu Gln
    50                  55                  60                  65
``` or having the formula V (SEQ ID NO: 15)

```
Ile Thr Tyr Thr Asp Cys Thr Glu Ser Gly Gln Asn Leu Cys Leu Cys      (V)
1               5                   10                  15

Glu Gly Ser Asn Val Cys Gly Lys Gly Asn Lys Cys Ile Leu Gly Ser
            20                  25                  30

Gln Gly Lys Asp Asn Gln Cys Val Thr Gly Glu Gly Thr Pro Lys Pro
        35                  40                  45

Gln Ser His Asn Gln Gly Asp Phe Glu Pro Ile Pro Glu Asp Ala Tyr Asp Glu.
    50                  55                  60                  65
```

HV3 and variants of HV3 which are characterized by a shortening of the primary structure by 1 or 2 amino acids at the N-terminus or by 18, 10, 9, 6, 4 or 2 amino acids at the C-terminus.

Particularly preferred desulphatohirudin compounds are those of formula I in which the Xaa groups are as defined under a) or the compound of formula III in which Xaa at 47 is Lys and Xaa at 63 is Tyr.

The most preferred hirudin is desulphatohirudin HV1 having the formula I in which Xaa at 27, 36 and 47 are each Lys, Xaa at 51 is His and Xaa at 62 is the peptide residue Glu-Tyr-Leu-Gln (SEQ ID NO:16).

Another embodiment of the invention relates to the hirudin variant refludan, or Leu-hirudin, also described as [Leu$^1$, Thr$^2$]-63-desulphatohirudin or lepirudin, which is described in sequence number 4 of European Patent No. EP-B 0 324 712 and in Formula VI (SEQ ID NO: 17).

A further embodiment relates to hirudin variants having delayed action (e.g. PEG-hirudin, described in European Patent No. EP 0 345 616). Another embodiment of the invention relates to hirudin and hirudin variants, which, compared to the natural isoforms or variants, are truncated at the N terminus and/or C terminus. In another embodiment of the invention, a hirudin variant has 80% or more homology (amino acid identity) to a natural isoform of hirudin.

The hirudins used in the present invention can be prepared synthetically, e.g., chemically or preferably by recombinant techniques, or by isolation from leeches.

According to the present invention the term "mutant" refers to proteins (muteins) exhibiting antithrombotic activity which differ from native hirudin or desulphatohirudin by simple or multiple mutations (cf. European Patent Nos. 352 227 and 352 228). The DNA coding for said mutants which can be prepared by methods known in the art e.g., site-directed mutagensis, is cloned and expressed in microbial hosts such as Escherichia coli and Saccharomyces cerevisiae.

Alternatively, hirudins that may be utitlized according to the present invention are hirudin fragments (i.e. those with at least the last 8 carboxyterminal amino acids, e.g. the fragment consisting of the last C-terminal amino acids of the known

```
Leu Thr Tyr Thr Asp Cys Thr Glu Ser Gly Gln Asn Leu Cys Leu Cys      (VI)
1               5                   10                  15

Glu Gly Ser Asn Val Cys Gly Gln Gly Asn Lys Cys Ile Leu Gly Ser
            20                  25                  30

Asp Gly Glu Lys Asn Gln Cys Val Thr Gly Glu Gly Thr Pro Lys Pro
        35                  40                  45

Gln Ser His Asn Asp Gly Asp Phe Glu Glu Ile Pro Glu Glu Tyr Leu Gln
    50                  55                  60                  65
``` sequence in hirudin), biosynthetic analogues of hirudin (e.g. those with up to 10 to 12 amino acids, some of which are commercially available), the protein NAPc2, and low molecular weight peptide-based thrombin inhibitors.

Preferred thrombin inhibitors include low molecular weight peptide-based thrombin inhibitors. The term "low molecular weight peptide-based thrombin inhibitors" will be well understood by one skilled in the art to include thrombin inhibitors with one to four peptide linkages, and/or with a molecular weight below 1000, and includes those described in the review paper by Claesson in Blood Coagul. Fibrin. (1994) 5,411, as well as those disclosed in U.S. Pat. No. 4,346,078; International Patent Applications WO 93/11152, WO 95/23609, WO 95/35309, WO 96/25426, WO 94/29336, WO 93/18060 and WO 95/01168; and European Patent Nos. 648 780, 468 231, 559 046, 641 779, 185 390, 526 877, 542 525, 195 212, 362 002, 364 344, 530 167, 293 881, 686 642, 669 317 and 601 459.

Preferred low molecular weight peptide-based thrombin inhibitors include those known collectively as the "gatrans". Particular gatrans which may be mentioned include HOOC—$CH_2$—(R)Cha-Pic-Nag-H (known as inogatran; see International Patent Application WO 93/11152 and the list of abbreviations therein) and HOOC—$CH_2$—(R)Cgl-Aze-Pab-H (known as melagatran; see International Patent Application WO 94/29336 and the list of abbreviations therein). Particularly preferred thrombin inhibitors include melagatran and ximelagatran. Other argentine derivatives may be useful in the present invention.

A novel class of synthetic peptides has been designed that inhibit the thrombin catalytic site and exhibit specificity for the anion-binding exosite (ABE) of alpha-thrombin. These peptides, called "hirulogs", consist of (i) an active-site specificity sequence with a restricted Arg-Pro scissile bond, (ii) a polymeric linker of glycyl residues from 6 to 18 A in length, and (iii) an ABE recognition sequence such as that in the hirudin C-terminus, such as but not limited to, Hirulog-1 [(D-Phe)-Pro-Arg-Pro-(Gly)4-Asn-Gly-Asp-Phe-Glu-Glu-Ile-Pro-Glu-Tyr-Leu] (SEQ ID NO:18); the synthetic C-terminal hirudin peptide S-Hir53-64; the pentapeptide (D-Phe)-Pro-Arg-Pro-Gly (SEQ ID NO:19); and bivalirudin.

The hirudin compounds used in the invention can be in the free form but also in the form of their salts. As they contain free amino group in several amino acid residues, the compounds can be in the form of acid addition salts. Suitable acid addition salts are in particular pharmacologically acceptable salts with conventional therapeutically acceptable acids. Representative inorganic acids are hydrohalic acids (such as hydrochloric acid), and also sulfuric acid, phosphoric acid and pyrophosphoric acid. Representative organic acids are in particular arenesulfonic acids (such as benzenesulfonic or p-toluenesulfonic acid), or lower alkanesulfonic acids (such as methanesulfonic acid), as well as carboxylic acids such as acetic acid, lactic acid, palmitic acid, stearic acid, malic acid, tartaric acid, ascorbic acid and citric acid. As, however, the compound used in the invention also contains free carboxyl groups in several amino acid residues, which carboxyl groups impart acidic character to the entire peptide, they can also be in the form of salts with inorganic or organic bases, e.g., sodium, potassium, calcium or magnesium salts, or also ammonium salts derived from ammonia or a pharmacologically acceptable organic nitrogen-containing base. However, as they contain at the same time free carboxyl groups and free amino groups, they can also be in the form of inner salts. Pharmacologically acceptable salts are preferred. A "pharmaceutically acceptable salt" is a salt that retains the biological effectiveness of the free acids and bases of the specified compound and that is not biologically or otherwise undesirable.

One problem in developing a dosage form containing hirudin is its poor stability in aqueous solutions and in powder form. The poor stability can be seen when hirudin is analyzed by chromatographic methods, such as reverse phase HPLC (RP-HPLC), MONO Q method, or the PROPAX method.

RP-HPLC method: A LiChroCART 125-4 column is used (Merck LiChrospher 100 RP-18 5 .mu.m). Solvent A is 0.5% ammonium acetate in acetonitrile/water (10:90), (v:v); solvent B is 0.5% ammonium acetate in acetonitrile/water (25:75). The elution is performed at 45° C. using a flow rate of 0.5 ml/min. The binary elution is a linear gradient starting at time zero with 23% solvent B and reaching 46% solvent B after 24 minutes. After 2 min at 70% solvent B the column is equilibrated for 7 min at 23% solvent B.

MONO Q METHOD: The stability of hirudin can be analysed by FPLC (fine protein liquid chromatography) using a Mono-Q column (10 μm particle size, 5.0×50 mm, purchased from Pharmacia). The method was developed by Ciba-Geigy, Basel. Solvent A is 50 mM $HCOONH_4$ in $H_2O$ pH 4.5, and solvent B is 50 mM $HCOONH_4$ in $H_2O$, pH 3.5. The elution is performed at room temperature (22° C.) using a flow rate of 1.4 ml/min. The binary elution for the first 5 min is at constant flow of 20% B, followed by a linear gradient from 20% B to 75% B over 10 minutes, and 2 minutes at 100% B after which the column is equilibrated for 2 minutes at the starting conditions of 20% B.

PROPAC METHOD: A recently published method for hirudin analysis can also be used (Tuong, A., et al., "Characterisation of the Deamidated Forms of Recombinant Hirudin" *Biochemistry*, 31:8291-8299 (1992)). In this method a ProPac PA1 anion-exchange column (250×4 mm i.d.) from Dionex is used. Solvent A is 20 mM Tris-HCl, pH 7.0 and solvent B is 0.5M NaCL in A. Isocrastic elution for 5 min at 28% is followed by a linear gradient from 28% B to 54% B over 60 minutes at a flow rate of 1.3 m/min.

Potassium phosphate can be used to increase the stability of hirudin (U.S. Pat. No. 6,436,901 B1). Accordingly, one embodiment of the present invention provides a freeze-dried pharmaceutical composition comprising hirudin, potassium phosphate and a sugar. A freeze-dried composition of the invention may be produced by forming an aqueous solution of the ingredients and then freeze-drying it in a conventional manner.

The potassium phosphate is preferably dipotassium hydrogen phosphate. It may be used, in the solution before freeze-drying, at a molarity of from 0.1 to 0.5, preferably from 0.1 to 0.3.

Suitable sugars include, but are not limited to, mannitol, trehalose, sucrose, sorbitol, fructose, glucose, maltose, lactose and dextran. The preferred sugars are mannitol and trehalose. The amount of sugar in the solution before freeze-drying may be such as to produce a concentration of from 5 to 50% (w/v) and preferably from 5 to 20% (w/v).

The solution before freeze-drying is preferably isotonic. The pH of the solution before freeze drying may be from 4 to 10, preferably from 6 to 9 and most preferably from 6.5 to 8. If desired a citrate buffer may be added to the solution before freeze-drying, e.g., by adding citric acid. The molarity of the citrate may be from 0.1 to 0.5, preferably from 0.1 to 0.3.

The concentration of hirudin in the solution before freeze-drying may be from 0.1 to 500 mg/ml, preferably from 20 to 250 mg/ml.

The freeze-dried product is stable for long periods of time without the need for refrigerated storage. In addition, after the product has been redissolved in water, the resulting solution is also stable for long periods although the stability in solution is not as good as the stability of the freeze-dried powder.

The solutions made by redissolving the freeze-dried product may be used in the production of standard ampoules, pre-filled double camber syringes, or multi-administration systems. The solutions may of course also be used immediately for administration.

The compounds of this invention may be in the form of a "pharmaceutically acceptable prodrug," i.e., a compound that may be converted under physiological conditions or by solvolysis to the specified compound or to a pharmaceutically acceptable salt of such compound. Prodrugs may be identified using routine techniques known in the art. Various forms of prodrugs are known in the art. For examples of such prodrug derivatives, see, for example, a) *Design of Prodrugs*, edited by H. Bundgaard, (Elsevier, 1985) and *Methods in Enzymology*, Vol. 42, p. 309-396, edited by K. Widder, et al. (Academic Press, 1985); b) *A Textbook of Drug Design and Development*, edited by Krogsgaard-Larsen and H. Bundgaard, Chapter 5 *"Design and Application of Prodrugs"*, by H. Bundgaard p. 113-191 (1991); c) H. Bundgaard, *Advanced Drug Delivery Reviews*, 8, 1-38 (1992); d) H. Bundgaard, et al., *Journal of Pharmaceutical Sciences*, 77:285 (1988); and e) N. Kakeya, et al., *Chem. Pharm. Bull.*, 32: 692 (1984), each of which is specifically incorporated herein by reference.

The amount of desulphatohirudin in the formulation is preferably a relatively low, effective single unit dose that may be repeatedly administered over time, e.g., over a period of days, weeks, or months. Of course, the actual amount in any unit dose and the administration schedule will depend upon a number of factors, such as the patient and the type of condition, disease, or disorder that is responsive to inhibition of angiogenesis. The amount of the desulphatohirudin, however, is a quantity that is effective to inhibit angiogenesis, but insufficient to cause substantial cellular death by a direct cytotoxic mechanism, in contrast to cellular death as a result of inhibition of angiogenesis. In the context of desulphatohirudin, the required amount at least partially inhibits the formation of new blood vessels.

Preferably, the effective angiogenesis-inhibiting amount of desulphatohirudin represents from about 0.0001 mg to about 200 mg desulphatohirudin per kilogram body weight of the patient, more preferably from about 0.0001 to about 120 mg desulphatohirudin per kilogram body weight of the patient, still more preferably from about 0.0001 mg to about 15 mg desulphatohirudin per kilogram body weight of the patient, yet still more preferably from about 0.5 mg to about 15 mg desulphatohirudin per kilogram body weight of the patient, and most preferably from about 1 mg to about 13 mg desulphatohirudin per kilogram body weight of the patient. In terms of weight percent, the formulations will preferably comprise the desulphatohirudin in an amount of from about 0.0001 wt. % to about 10 wt. %, more preferably from about 0.001 wt. % to about 1 wt. %, and most preferably from about 0.01 wt. % to about 0.5 wt. %.

B. Solvent

In order to use a compound, or a pharmaceutically acceptable salt or in vivo cleavable prodrug thereof, for the therapeutic treatment (including prophylactic treatment) of mammals including humans, it is normally formulated in accordance with standard pharmaceutical practice as a pharmaceutical composition. According to one embodiment of the invention there is provided a pharmaceutical composition that comprises desulphatohirudin or a desulphatohirudin variant, or a pharmaceutically acceptable salt or in vivo cleavable prodrug thereof, as defined hereinbefore in association with a pharmaceutically acceptable solvent or carrier. By "pharmaceutically acceptable" solvent or carrier is meant a pharmaceutical vehicle comprised of a material that is not biologically or otherwise undesirable, i.e., the material may be administered to an individual along with the desulphatohirudin without causing any undesirable biological effects or interacting in a deleterious manner with any of the other components of the pharmaceutical formulation in which it is contained.

Suitable solvents include, without limitation: alcohols, e.g., monohydric alcohols such as 1-butanol, 2-butanol, 3-methyl-1-butanol, 2-methyl-1-propanol, and ethanol, as well as polyhydric alcohols such as propylene glycol; ethyl ether; ethyl formate; ethyl acetate; methyl acetate; isobutyl acetate; isopropyl acetate; methylethyl ketone; dimethylacetamide (DMA); 1,1-dimethyloxymethane; 2,2-dimethyloxypropane; dimethyl sulfoxide (DMSO); and the like. The solvent may be an organic solvent or an inorganic solvent. Furthermore, the solvent may be aqueous or nonaqueous. As will be readily appreciated by one of ordinary skill in the art, the choice of solvent will depend on the desired solubility, the nature of the desulphatohirudin, and the desired release characteristics.

The amount of solvent present in the formulation will vary depending on the type of tumor (solid or soft), the solubility of desulphatohirudin, the solvent chosen, and the desired form of the formulation (e.g., solution, suspension, etc.). Those of ordinary skill in the art routinely consider such factors in determining the appropriate amount of a solvent in a pharmaceutical formulation. Thus, the amount of solvent included in the pharmaceutical formulation may be established by those skilled in the art without undue experimentation. In one embodiment, the amount of solvent contained in the formulation is from about 0.01% by volume to about 50% by volume (v/v) of formulation.

In one embodiment, the desulphatohirudin (optionally together with a solvent) is added to a carrier, i.e., a solution such as but not limited to a sodium chloride solution (e.g., normal saline), a dextrose solution, lactated Ringer's solution, water, or a mixture thereof. Carriers may include excipients and other additives such as diluents, detergents, coloring agents, wetting or emulsifying agents, pH buffering agents, preservatives, and the like. The desulphatohirudin, solvent, and any additional components are added to the carrier and mixed.

C. Formulations

The pharmaceutical formulations of the present invention are not limited with regard to the particular form used. A nonlimiting list of preferred delivery forms of the present invention includes solutions, suspensions, dispersions, emulsions, and controlled release formulations such as microspheres. For systemic administration, solutions and suspensions are preferred. For local administration, any delivery form, e.g., solution, suspension, dispersion, emulsion, or microspheres, may be used.

In general, the pharmaceutical formulation may include one or more additional components. Such additional components include, for example, antimicrobials, buffers, antioxidants, tonicity-adjusting agents, and detergents. Antimicrobial agents are used to deter the growth of microorganisms, particularly in multiple dose formulations (i.e., formulation for a multiple dose vial). Suitable antimicrobial agents include phenylmercuric nitrate, thimerosal, benzethonium chloride, benzalkonium chloride, phenol, cresol, chlorobutanol, and combinations thereof. Buffers are used primarily to stabilize a solution against potential chemical degradation resulting from a change in the formulation's pH. Suitable buffers include acid salts of citrates, acetates, and phosphates. Antioxidants are used for preservation, as many drugs are susceptible to degradation through oxidation. Examples of antioxidants include sodium bisulfite, acetone sodium bisulfite, sodium formaldehyde, sulfoxylate, thiourea, ascorbic acid, sodium salt of ethylenediamine tetraacetic acid, and storage in an inert gas (e.g., nitrogen). Tonicity-adjusting agents are used to control tonicity to ensure that the resulting formulation is not excessively hypotonic or hypertonic relative to the physiological state. Examples of tonicity agents include electrolytes (e.g. sodium chloride) and mono- or disaccharides (e.g., dextrose for monosaccharides). Examples of detergents include, for example, anionic detergents; nonionic detergents, e.g., polyoxyethylated sorbitans (available under the TWEEN™ name from ICI Americas, Inc.); sorbitan esters; polysorbates;,polyoxyethylene ethers (e.g., available under the TRITON™ name from Union Carbide Corp., Midland Mich.); cationic and zwitterionic detergents; and combinations thereof.

The amounts of additional components that are not active agents will vary depending on the solvents chosen, desired form of the formulation, and other factors. Those of ordinary skill in the art routinely consider such factors. Thus, the amount of any particular additional component can be established by those skilled in the art without undue experimentation. Typically, the amount of any such component preferably does not exceed 10% by volume of the total formulation.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, or intramuscular dosing or as a suppository for rectal dosing). For example, compositions intended for oral use may contain, for example, one or more coloring, sweetening, flavoring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 µm or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulations, see Chapter 25.2 in Volume 5 of Comprehensive Medicinal Chemistry (Corwin Hansch; Chairman of Editorial Board), Pergamon Press 1990, which is specifically incorporated herein by reference.

The amount of a compound of this invention that is combined with one or more excipients to produce a single dosage form will necessarily vary depending upon the host treated and the particular route of administration. For example, a formulation intended for oral administration to humans may contain, for example, from 0.5 mg to 2 g of desulphatohirudin compounded with an appropriate and convenient amount of excipients which may vary from about 5 to about 98 percent by weight of the total composition. Dosage unit forms will generally contain about 1 mg to about 500 mg of an active ingredient. For further information on routes of administration and dosage regimes, see Chapter 25.3 in Volume 5 of Comprehensive Medicinal Chemistry (Corwin Hansch; Chairman of Editorial Board), Pergamon Press 1990, which is specifically incorporated herein by reference.

The pharmaceutical formulations of the present invention may be sustained-release formulations. The term "sustained release" as used herein refers to a drug formulation that provides for gradual release of a drug over an extended period of time, and that preferably, although not necessarily, results in substantially constant drug levels at the desired site over an extended period of time. That is, the formulation would release the desulphatohirudin over an extended period of time relative to an immediate-release or nonsustained-release formulation. For example, in one embodiment the pharmaceutical formulations of the present invention release desulphatohirudin over a time of from about 4 hours to about 24 hours.

Sustained-release formulations generally include one or more components designed to slow or control the release of the desulphatohirudin over time. The invention is not limited with regard to the particular component(s) used to effect sustained release, so long as the component or components are pharmaceutically acceptable. Preferred sustained-release components include polysaccharides, salts of polysaccharides, microspheres of polysaccharides, dextrins, gums, celluloses, gels, silicones, liposomes, and combinations thereof. It is particularly preferred that the sustained-release component be a polysaccharide. Examples of suitable polysaccharides include, but are not limited to, chitin (poly-N-acetyl-D-glucosamine), chitosan (deacetylated chitin), and combinations thereof. Derivatives of these carriers are contemplated as well, including, for example, derivatives formed by adding or removing sugar molecules (i.e. by increasing or decreasing the weight average molecular weight of the carrier). In one embodiment, the carriers have a weight average molecular weight of about 500 daltons to about 100,000 daltons, more preferably of about 10,000 daltons to about 60,000 daltons.

The component providing sustained release can be covalently bonded to the desulphatohirudin, thereby providing a sustained-release conjugate. For example, chitin may be covalently bound to desulphatohirudin. Methods for producing these conjugates are well known to those skilled in the art, and are described in detail in the pertinent texts and literature.

The amount of the component or components providing sustained release will depend on several factors, such as whether the formulation is intended to contain a single dose or multiple doses, and the injectability (e.g., viscosity) of the resulting formulation. In addition, the amount should be considered in light of the environment of the target area in which the pharmaceutical formulation will be administered. For example, it is desirable that low density organs, e.g., the prostate, brain, and bladder, receive a low viscosity formulation, whereas dense tissue, e.g., solid tumors and breast tumors, receive a high viscosity pharmaceutical formulation. Those of ordinary skill in the art routine consider these and other factors in providing sustained-release formulations.

Generally, the total amount of a sustained-release component in the formulation is preferably between from about 0.01% w/v to about 50% w/v of the total formulation. It is particularly preferred that the biocompatible carrier is present in an amount of from about 0.5% w/v to about 30% w/v.

II. Methods of Treatment

The present invention also provides a method for inhibiting angiogenesis in a patient in need thereof comprising administering to the patient an effective angiogenesis-inhibiting amount of desulphatohirudin. The method is used to treat a patient suffering from a condition, disease, or disorder that is treatable by at least partial inhibition of angiogenesis. In general, patients suffering from a neoplastic disease, i.e., a cellular proliferative disease, benefit from administration of the present compositions. Generally, cellular proliferative diseases include not only sarcomas, carcinomas, lymphomas, and malignant melanomas, but also noncancerous melanomas and other benign growths caused by rapidly dividing cells.

Nonlimiting examples of cellular proliferative diseases for which the present invention is suited include adrenocortical cancer, bladder cancer, bone cancer, brain cancer, breast cancer, cervical cancer, colon cancer, colorectal cancer, endometrial cancer, esophogeal cancer, eye cancer, gallbladder cancer, gastric cancer, head and neck cancer, laryngeal cancer, liver cancer, lung cancer, melanoma, myeloproliferative disorders such as myeloma, neck cancer, nonmelanoma skin cancer, ovarian cancer, prostate cancer, pancreatic cancer, rectal cancer, and testicular cancer. Diseases for which the present invention is particularly well suited to treat include those diseases selected from the group consisting of brain cancer, bladder cancer, breast cancer, colon cancer, colorectal cancer, rectal cancer, head and neck cancer, liver cancer, lung cancer myeloma, prostate cancer, and ovarian cancer.

Further, included within the scope of the present invention is the co-administration of desulphatohirudin with an anticancer agent or a cytotoxic agent. Such agents suitably include, but are not limited to, antimetabolites (e.g., 5-fluoro-uracil, methotrexate, fludarabine), antimicrotubule agents (e.g., vincristine, vinblastine, taxanes such as paclitaxel, docetaxel), an alkylating agent (e.g., cyclophasphamide, melphalan, biochoroethylnitrosurea, hydroxyurea), platinum agents (e.g. cisplatin, carboplatin, oxaliplatin, JM-216, CI-973), anthracyclines (e.g., doxrubicin, daunorubicin), antibiolitics (e.g., mitomycin, idarubicin, adriamycin, daunomycin), topoisomerase inhibitors (e.g., etoposide, camptothecins) or any other cytotoxic agents. (estramustine phosphate, prednimustine). It is anticipated that desulphatohirudin used in combination with various anticancer drugs can give rise to a significantly enhanced cytotoxic effect on cancerous cells, thus providing an increased therapeutic effect. Specifically, a significantly increased growth-inhibitory effect can be obtained utilizing lower concentrations of the anticancer drugs compared to the treatment regimes in which the drugs are used alone. Thus, there is the potential to provide therapy wherein adverse side effects associated with the anticancer drugs are considerably reduced than normally observed with the anticancer drugs used alone in larger doses. Possible dose ranges of these co-administered anticancer agents are about 0.1 to 20 mg/kg/day.

The term "co-administration" is meant to refer to any administration route in which two or more agents (i.e., desulphatohirudin and one or more additional anticancer or cytotoxic agents) are administered to a patient or subject. For example, the agents may be administered together, or before or after each other. The agents may be administered by different routes, e.g., one agent may be administered intravenously while the second agent is administered intramuscularly, intravenously or orally. The agents may be administered simultaneously or sequentially, as long as they are given in a manner sufficient to allow both agents to achieve effective concentrations in the body. The agents also may be in an admixture, as, for example, in a single tablet. In sequential administration, one agent may directly follow administration of the other or the agents may be give episodically, i.e., one can be given at one time followed by the other at a later time, typically within a week. An example of a suitable co-administration regimen is where desulphatohirudin is administered from 0.5 to 7 days prior to administration of a cytotoxic agent.

According to the present invention, suitable methods of administering the therapeutic composition of the present invention to a patient include any route of in vivo administration that is suitable for delivering the composition into a patient. The preferred routes of administration will be apparent to those of skill in the art, depending on the type of condition to be prevented or treated, and/or the target cell population. Preferred methods of in vivo administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, intraarticular administration, intraventricular administration, inhalation (e.g., aerosol), intracranial, intraspinal, intraocular, intranasal, oral, bronchial, rectal, topical, vaginal, urethral, pulmonary administration, impregnation of a catheter, and direct injection into a tissue.

Parenteral administration may be carried out in any number of ways, but it is preferred that the use of a syringe, catheter, or similar device, be used to effect parenteral administration of the formulations described herein. The formulation may be injected systemically such that the desulphatohirudin travels substantially throughout the entire bloodstream.

In addition, the formulation may also be injected locally to a target site, i.e., injected to a specific portion of the body for which inhibition of angiogenesis is desired. An advantage of local administration via injection is that it limits or avoids exposure of the entire body to the desulphatohirudin. It must be noted that in the present context, the term local administration includes regional administration, e.g., administration of a formulation directed to a portion of the body through delivery to a blood vessel serving that portion. Local delivery may be direct, i.e., intratumoral. Local delivery may also be nearly direct, i.e., intralesional or intraperitoneal, that is, to an area that is sufficiently close to a tumor so that the desulphatohirudin exhibits the desired pharmacological activity. Thus, when local delivery is desired, the pharmaceutical formulations are preferably delivered intralesionally, intratumorally, or intraperitoneally.

It is intended that, by local delivery of the presently described pharmaceutical formulations, a higher concentration of the desulphatohirudin may be retained at the target site. There are several advantages to having high concentrations delivered directly at the target site. First, since the desulphatohirudin is localized, there is less potential for toxicity to the patient since minimal systemic exposure occurs. Second, drug efficacy is improved since the target site is exposed to higher concentrations of drug. Third, relatively fast delivery ensures both solubility of the drug and little or no degradation of the desulphatohirudin before reaching the target site. Fourth, the method is relatively noninvasive, which is ideal for unresectable tumors such as brain tumors, liver tumors, and pancreatic tumors.

With local administration, it is preferred that the pharmaceutical formulations of the present invention be directed to the target area with the assistance of computerized tomography (CT), ultrasound, or similar method in order to ensure correct placement. Once the initial dose is administered, the patient may be given other doses either immediately or after a period of time. Such a dosing schedule is easily determined by one of ordinary skill in the art once the nature of the condition, disorder, or disease, strength of the patient, expected effects of the formulation, and so forth, are taken into consideration.

The amount of desulphatohirudin administered will, of course, be dependent on the subject being treated, the subject's weight, the manner of administration, and the judgment of the prescribing physician. The amount of desulphatohirudin administered, however, will be an effective angiogenesis-inhibiting amount. Preferably, the desulphatohirudin is administered in an amount of from about 0.0001 mg/kg to about 200 mg/kg (milligrams of drug per kilogram body weight of the patient), more preferably from about 0.0001 mg/kg to 120 mg/kg, still more preferably from about 0.0001 mg/kg to about 15 mg/kg, yet still more preferably from about 0.5 mg/kg to about 15 mg/kg, and most preferably from about 1 mg/kg to about 13 mg/kg. Depending on the patient's response, additional dosages within this range may be administered.

The size of the dose for therapeutic or prophylactic purposes of desulphatohirudin will naturally vary according to the nature and severity of the conditions, the age and sex of the animal or patient and the route of administration, according to well known principles of medicine. For example, the method may comprise at least one of an hourly administration, a daily administration, a weekly administration, or a monthly administration of one or more compositions described herein.

Throughout this application, various patents are referenced by number and publications are referenced by author and date. The disclosures of these patents and publications are hereby incorporated by reference in their entireties into this application in order to more fully describe the state of the art as known to those skilled therein as of the date of this invention described and claimed herein.

The foregoing description is considered as illustrative only of the principles of the invention. Further, since numerous modifications and changes will readily occur to those skilled in the art, it is not desired to limit the invention to the exact construction and process shown as described above. Accordingly, all suitable modifications and equivalents may be resorted to falling within the scope of the invention as defined by the claims that follow. The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A method of effecting regression of tumor mass and size in a metastasized pancreatic tumor in a subject, the method comprising administering to the subject a pharmaceutical formulation comprising an effective amount of a desulphato-hirudin variant selected from the group consisting of a) SEQ ID NO:1 wherein Xaa at 27, 36 and 47 are each Lys, Xaa at 51 is His and Xaa at 62-65 is the peptide residue Glu-Tyr-Leu-Gln (SEQ ID NO:2) Xaa at 66 not present, b) SEQ ID NO:1 wherein Xaa at 27 is Ile or Glu and Xaa at 36, 47, 51 and 62-66 are as defined in a), c) SEQ ID NO:1 wherein Xaa at 36 is Ile or Glu and Xaa at 27, 47, 51 and 62-66 are as defined in a), d) SEQ ID NO:1 wherein Xaa at 47 is Ile or Glu and Xaa at 27, 36, 51 and 62-66 are as defined in a), and e) SEQ ID NO:1 wherein Xaa at 51 is Leu or Asp and Xaa at 27, 36, 47 and 62-66 are as defined in a), to effect regression of the metastasized pancreatic tumor in the subject.

2. The method of claim 1, wherein said desulphatohirudin variant is SEQ ID NO. 1, wherein Xaa at 27, 36 and 47 are each Lys, Xaa at 51 is His and Xaa at 62-65 is the peptide residue Glu-Tyr-Leu-Gln (SEQ ID NO:2) Xaa at 66 not present.

3. The method of claim 1 wherein the pharmaceutical formulation is administered via injection.

4. The method of claim 3, wherein the pharmaceutical formulation is systemically injected.

5. The method of claim 3, wherein the pharmaceutical formulation is locally injected.

6. The method of claim 1, wherein the desulphatohirudin variant is co-administered with a cytotoxic agent comprising an anthracycline selected from the group consisting of doxorubicin and daunorubicin and the co-administration results in increased therapeutic effect as compared to administration of the cytotoxic agent alone.

7. The method of claim 1, wherein the pharmaceutical formulation further includes potassium phosphate.

8. The method of claim 1, wherein the pharmaceutical formulation further includes a divalent or trivalent metal ion.

9. The method of claim 8, wherein the pharmaceutical formulation further includes a sugar.

10. The method of claim 1, wherein the pharmaceutical formulation provides a sustained-release profile in vivo.

11. A method of treating a prevascularized metastasized pancreatic tumor in a subject, comprising administering to the subject a pharmaceutical formulation consisting essentially of an effective amount of a desulphatohirudin variant selected from the group consisting of a) SEQ ID NO:1 wherein Xaa at 27, 36 and 47 are each Lys, Xaa at 51 is His and Xaa at 62-65 is the peptide residue Glu-Tyr-Leu-Gln (SEQ ID NO:2) Xaa at 66 not present, b) SEQ ID NO:1 wherein Xaa at 27 is Ile or Glu and Xaa at 36, 47, 51 and 62-66 are as defined in a), c) SEQ ID NO:1 wherein Xaa at 36 is Ile or Glu and Xaa at 27, 47, 51 and 62-66 are as defined in a), d) SEQ ID NO:1 wherein Xaa at 47 is Ile or Glu and Xaa at 27, 36, 51 and 62-66 are as defined in a), and e) SEQ ID NO:1 wherein Xaa at 51 is Leu or Asp and Xaa at 27, 36, 47 and 62-66 are as defined in a), to effect regression of the pancreatic tumor in the subject.

12. The method of claim 11, wherein said desulphatohirudin is SEQ ID NO. 1, wherein Xaa at 27, 36 and 47 are each Lys, Xaa at 51 is His and Xaa at 62-65 is the peptide residue Glu-Tyr-Leu-Gln (SEQ ID NO:2) Xaa at 66 not present.

13. The method of claim 11, wherein the desulphatohirudin variant is co-administered with a cytotoxic agent comprising an anthracycline selected from the group consisting of doxorubicin and daunorubicin such that the co-administration results in increased therapeutic effect as compared to administration of the cytotoxic agent alone.

* * * * *

SEQUENCE LISTING

<160> NUMBER OF SEQ ID NOS: 19

<210> SEQ ID NO 1
<211> LENGTH: 66
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (27)..(66)
<223> OTHER INFORMATION: a) Xaa at 27, 36 and 47 are each Lys, Xaa at 51
      is His, Xaa at 62-65 are Glu-Tyr-Leu-Gln, and Xaa at 66 is absent
<220> FEATURE:
<221> NAME/KEY: MISC_FEATURE
<222> LOCATION: (27)..(66)
<223> OTHER INFORMATION: b) Xaa at 27 is Ile or Glu, and Xaa at 36, 47,
      51 and 62-66 are as defined in a)
<220> FEATURE:
<221> NAME/KEY: MISC_FEATURE
<222> LOCATION: (27)..(66)
<223> OTHER INFORMATION: c) Xaa at 36 is Ile or Glu, and Xaa at 27, 47,
      51 and 62-66 are as defined in a)
<220> FEATURE:
<221> NAME/KEY: MISC_FEATURE
<222> LOCATION: (27)..(66)
<223> OTHER INFORMATION: d) Xaa at 47 is Ile or Glu, and Xaa at 27, 36,
      51 and 62-66 are as defined in a)
<220> FEATURE:
<221> NAME/KEY: MISC_FEATURE
<222> LOCATION: (27)..(66)
<223> OTHER INFORMATION: e) Xaa at 51 is Leu or Asp, and Xaa at 27, 36,
      47 and 62-66 are as defined in a), or
<220> FEATURE:
<221> NAME/KEY: MISC_FEATURE
<222> LOCATION: (27)..(66)
<223> OTHER INFORMATION: f1), f2) and f3), where
<220> FEATURE:
<221> NAME/KEY: MISC_FEATURE
<222> LOCATION: (27)..(66)
<223> OTHER INFORMATION: f1) Any one or all of Xaa at 64-66 can either
      be present or absent
<220> FEATURE:
<221> NAME/KEY: MISC_FEATURE
<222> LOCATION: (27)..(66)
<223> OTHER INFORMATION: f2) Xaa at 62-66 are Glu-Tyr, Glu-Tyr-Leu,
      Glu-Asp-Leu-Gln, Glu-Glu-Leu-Gln, Glu-Tyr-Lys-Arg,
      Glu-Asp-Lys-Arg, Glu-Lys-Leu-Gln, Ser-Phe-Arg-Tyr,
      Trp-Glu-Leu-Arg, Glu-Tyr-Leu-Gln-Pro or Glu-Tyr-Leu-Gln-Arg
<220> FEATURE:
<221> NAME/KEY: MISC_FEATURE
<222> LOCATION: (27)..(66)
<223> OTHER INFORMATION: f3)  Xaa at 27, 36, 47 and 51 are as defined in
      a)

<400> SEQUENCE: 1

Val Val Tyr Thr Asp Cys Thr Glu Ser Gly Gln Asn Leu Cys Leu Cys
1               5                   10                  15

Glu Gly Ser Asn Val Cys Gly Gln Gly Asn Xaa Cys Ile Leu Gly Ser
            20                  25                  30

Asp Gly Glu Xaa Asn Gln Cys Val Thr Gly Glu Gly Thr Pro Xaa Pro
        35                  40                  45

Gln Ser Xaa Asn Asp Gly Asp Phe Glu Glu Ile Pro Glu Xaa Xaa Xaa
    50                  55                  60

Xaa Xaa
65

<210> SEQ ID NO 2
<211> LENGTH: 4
<212> TYPE: PRT

```
<213> ORGANISM: Artificial sequence
<220> FEATURE:
<223> OTHER INFORMATION: Synthetic peptide

<400> SEQUENCE: 2

Glu Tyr Leu Gln
1

<210> SEQ ID NO 3
<211> LENGTH: 4
<212> TYPE: PRT
<213> ORGANISM: Artificial sequence
<220> FEATURE:
<223> OTHER INFORMATION: Synthetic peptide

<400> SEQUENCE: 3

Glu Asp Leu Gln
1

<210> SEQ ID NO 4
<211> LENGTH: 4
<212> TYPE: PRT
<213> ORGANISM: Artificial sequence
<220> FEATURE:
<223> OTHER INFORMATION: Synthetic peptide

<400> SEQUENCE: 4

Glu Glu Leu Gln
1

<210> SEQ ID NO 5
<211> LENGTH: 4
<212> TYPE: PRT
<213> ORGANISM: Artificial sequence
<220> FEATURE:
<223> OTHER INFORMATION: Synthetic peptide

<400> SEQUENCE: 5

Glu Tyr Lys Arg
1

<210> SEQ ID NO 6
<211> LENGTH: 4
<212> TYPE: PRT
<213> ORGANISM: Artificial sequence
<220> FEATURE:
<223> OTHER INFORMATION: Synthetic peptide

<400> SEQUENCE: 6

Glu Asp Lys Arg
1

<210> SEQ ID NO 7
<211> LENGTH: 4
<212> TYPE: PRT
<213> ORGANISM: Artificial sequence
<220> FEATURE:
<223> OTHER INFORMATION: Synthetic peptide

<400> SEQUENCE: 7

Glu Lys Leu Gln
1

<210> SEQ ID NO 8
<211> LENGTH: 4
<212> TYPE: PRT
<213> ORGANISM: Artificial sequence
```

```
<220> FEATURE:
<223> OTHER INFORMATION: Synthetic peptide

<400> SEQUENCE: 8

Ser Phe Arg Tyr
1

<210> SEQ ID NO 9
<211> LENGTH: 4
<212> TYPE: PRT
<213> ORGANISM: Artificial sequence
<220> FEATURE:
<223> OTHER INFORMATION: Synthetic peptide

<400> SEQUENCE: 9

Trp Glu Leu Arg
1

<210> SEQ ID NO 10
<211> LENGTH: 5
<212> TYPE: PRT
<213> ORGANISM: Artificial sequence
<220> FEATURE:
<223> OTHER INFORMATION: Synthetic peptide

<400> SEQUENCE: 10

Glu Tyr Leu Gln Pro
1               5

<210> SEQ ID NO 11
<211> LENGTH: 5
<212> TYPE: PRT
<213> ORGANISM: Artificial sequence
<220> FEATURE:
<223> OTHER INFORMATION: Synthetic peptide

<400> SEQUENCE: 11

Glu Tyr Leu Gln Arg
1               5

<210> SEQ ID NO 12
<211> LENGTH: 65
<212> TYPE: PRT
<213> ORGANISM: Artificial sequence
<220> FEATURE:
<223> OTHER INFORMATION: Synthetic polypeptide

<400> SEQUENCE: 12

Leu Thr Tyr Thr Asp Cys Thr Glu Ser Gly Gln Asn Leu Cys Leu Cys
1               5                   10                  15

Glu Gly Ser Asn Val Cys Gly Gln Gly Asn Lys Cys Ile Leu Gly Ser
            20                  25                  30

Asp Gly Glu Lys Asn Gln Cys Val Thr Gly Glu Gly Thr Pro Lys Pro
        35                  40                  45

Gln Ser His Asn Asp Gly Asp Phe Glu Glu Ile Pro Glu Glu Tyr Leu
    50                  55                  60

Gln
65

<210> SEQ ID NO 13
<211> LENGTH: 65
<212> TYPE: PRT
<213> ORGANISM: Artificial sequence
<220> FEATURE:
<223> OTHER INFORMATION: Synthetic polypeptide
```

```
<220> FEATURE:
<221> NAME/KEY: MISC_FEATURE
<222> LOCATION: (47)..(63)
<223> OTHER INFORMATION: a) Xaa at 47 is Asn, and Xaa at 63 is Tyr
<220> FEATURE:
<221> NAME/KEY: MISC_FEATURE
<222> LOCATION: (47)..(63)
<223> OTHER INFORMATION: b) Xaa at 47 is Lys, Arg or His, and Xaa at 63
      is Tyr, or
<220> FEATURE:
<221> NAME/KEY: MISC_FEATURE
<222> LOCATION: (47)..(63)
<223> OTHER INFORMATION: c) Xaa at 47 is Asn, and Xaa at 63 is Glu or
      Asp

<400> SEQUENCE: 13

Ile Thr Tyr Thr Asp Cys Thr Glu Ser Gly Gln Asn Leu Cys Leu Cys
1               5                   10                  15

Glu Gly Ser Asn Val Cys Gly Lys Gly Asn Lys Cys Ile Leu Gly Ser
            20                  25                  30

Asn Gly Lys Gly Asn Gln Cys Val Thr Gly Glu Gly Thr Pro Xaa Pro
        35                  40                  45

Glu Ser His Asn Asn Gly Asp Phe Glu Glu Ile Pro Glu Glu Xaa Leu
    50                  55                  60

Gln
65

<210> SEQ ID NO 14
<211> LENGTH: 65
<212> TYPE: PRT
<213> ORGANISM: Artificial sequence
<220> FEATURE:
<223> OTHER INFORMATION: Synthetic polypeptide

<400> SEQUENCE: 14

Val Val Tyr Thr Asp Cys Thr Glu Ser Gly Gln Asn Leu Cys Leu Cys
1               5                   10                  15

Glu Gly Ser Asn Val Cys Gly Lys Gly Asn Lys Cys Ile Leu Gly Ser
            20                  25                  30

Asn Gly Lys Gly Asn Gln Cys Val Thr Gly Glu Gly Thr Pro Asn Pro
        35                  40                  45

Glu Ser His Asn Asn Gly Asp Phe Glu Glu Ile Pro Glu Glu Tyr Leu
    50                  55                  60

Gln
65

<210> SEQ ID NO 15
<211> LENGTH: 66
<212> TYPE: PRT
<213> ORGANISM: Artificial sequence
<220> FEATURE:
<223> OTHER INFORMATION: Synthetic polypeptide

<400> SEQUENCE: 15

Ile Thr Tyr Thr Asp Cys Thr Glu Ser Gly Gln Asn Leu Cys Leu Cys
1               5                   10                  15

Glu Gly Ser Asn Val Cys Gly Lys Gly Asn Lys Cys Ile Leu Gly Ser
            20                  25                  30

Gln Gly Lys Asp Asn Gln Cys Val Thr Gly Glu Gly Thr Pro Lys Pro
        35                  40                  45

Gln Ser His Asn Gln Gly Asp Phe Glu Pro Ile Pro Glu Asp Ala Tyr
    50                  55                  60
```

```
<210> SEQ ID NO 16
<211> LENGTH: 4
<212> TYPE: PRT
<213> ORGANISM: Artificial sequence
<220> FEATURE:
<223> OTHER INFORMATION: Synthetic peptide

<400> SEQUENCE: 16

Glu Tyr Leu Gln
1

<210> SEQ ID NO 17
<211> LENGTH: 65
<212> TYPE: PRT
<213> ORGANISM: Artificial sequence
<220> FEATURE:
<223> OTHER INFORMATION: Synthetic polypeptide

<400> SEQUENCE: 17

Leu Thr Tyr Thr Asp Cys Thr Glu Ser Gly Gln Asn Leu Cys Leu Cys
1               5                  10                  15

Glu Gly Ser Asn Val Cys Gly Gln Gly Asn Lys Cys Ile Leu Gly Ser
            20                  25                  30

Asp Gly Glu Lys Asn Gln Cys Val Thr Gly Glu Gly Thr Pro Lys Pro
        35                  40                  45

Gln Ser His Asn Asp Gly Asp Phe Glu Glu Ile Pro Glu Glu Tyr Leu
    50                  55                  60

Gln
65

<210> SEQ ID NO 18
<211> LENGTH: 19
<212> TYPE: PRT
<213> ORGANISM: Artificial sequence
<220> FEATURE:
<223> OTHER INFORMATION: Synthetic peptide

<400> SEQUENCE: 18

Phe Pro Arg Pro Gly Gly Gly Gly Asn Gly Asp Phe Glu Glu Ile Pro
1               5                  10                  15

Glu Tyr Leu

<210> SEQ ID NO 19
<211> LENGTH: 5
<212> TYPE: PRT
<213> ORGANISM: Artificial sequence
<220> FEATURE:
<223> OTHER INFORMATION: Synthetic peptide

<400> SEQUENCE: 19

Phe Pro Arg Pro Gly
1               5
```